United States Patent [19]

Apley et al.

[11] 4,442,720

[45] Apr. 17, 1984

[54] SAMPLING DEVICE FOR WITHDRAWING A REPRESENTATIVE SAMPLE FROM SINGLE AND MULTI-PHASE FLOWS

[75] Inventors: Walter J. Apley, Pasco; William C. Cliff; James M. Creer, both of Richland, all of Wash.

[73] Assignee: The United States of America as represented by the United States Department of Energy, Washington, D.C.

[21] Appl. No.: 456,146

[22] Filed: Jan. 6, 1983

Related U.S. Application Data

[63] Continuation of Ser. No. 173,247, Jul. 29, 1980, abandoned.

[51] Int. Cl.³ .............................................. G01N 1/26
[52] U.S. Cl. ............................... 73/863.31; 73/863.51
[58] Field of Search ........... 73/863.51, 863.54, 863.31, 73/863.58, 861.66

[56] References Cited

U.S. PATENT DOCUMENTS

| | | | |
|---|---|---|---|
| 1,255,622 | 2/1918 | McFarland | 73/861.66 |
| 1,494,855 | 5/1924 | Macmichael | 73/863.03 |
| 2,452,224 | 10/1948 | Collett, Jr. | 73/863.58 |
| 3,066,539 | 12/1962 | Coker et al. | 73/863.54 |
| 3,511,099 | 5/1970 | Harsha | 73/863.31 |
| 3,673,866 | 7/1972 | Alperovich et al. | 73/861.65 |
| 3,765,226 | 10/1973 | Strickland | 73/863.58 |
| 3,803,921 | 4/1974 | Dieterich | 73/863.51 |
| 3,842,678 | 10/1974 | DeBaum et al. | 73/863.58 |
| 3,859,842 | 1/1975 | Bosch | 73/863.03 |
| 3,965,748 | 6/1976 | Boubel et al. | 73/863.03 |
| 4,082,004 | 4/1978 | Weber et al. | 73/863.54 |
| 4,215,565 | 8/1980 | Zanker | 73/863.61 |

FOREIGN PATENT DOCUMENTS

| | | | |
|---|---|---|---|
| 718766 | 2/1942 | Fed. Rep. of Germany | 73/863.31 |
| 54-39189 | 3/1979 | Japan | 73/863.03 |

OTHER PUBLICATIONS

Schraub, "Isokenetic Probe and Other Two Phase Sampling Devices: A Survey", 11th National ASME/AICHE Heat Conference, pp. 47-57, 1969.
Lahey et al., "Mass Flux & Enthalpy Distribution etc.", Journal of Heat Transfer 93, 197-209, May 1971.

*Primary Examiner*—S. Clement Swisher
*Attorney, Agent, or Firm*—John M. Albrecht; Sandra B. Weiss; Michael F. Esposito

[57] ABSTRACT

A fluid stream sampling device has been developed for the purpose of obtaining a representative sample from a single or multi-phase fluid flow. This objective is carried out by means of a probe which may be inserted into the fluid stream. Individual samples are withdrawn from the fluid flow by sampling ports with particular spacings, and the sampling parts are coupled to various analytical systems for characterization of the physical, thermal, and chemical properties of the fluid flow as a whole and also individually.

12 Claims, 6 Drawing Figures

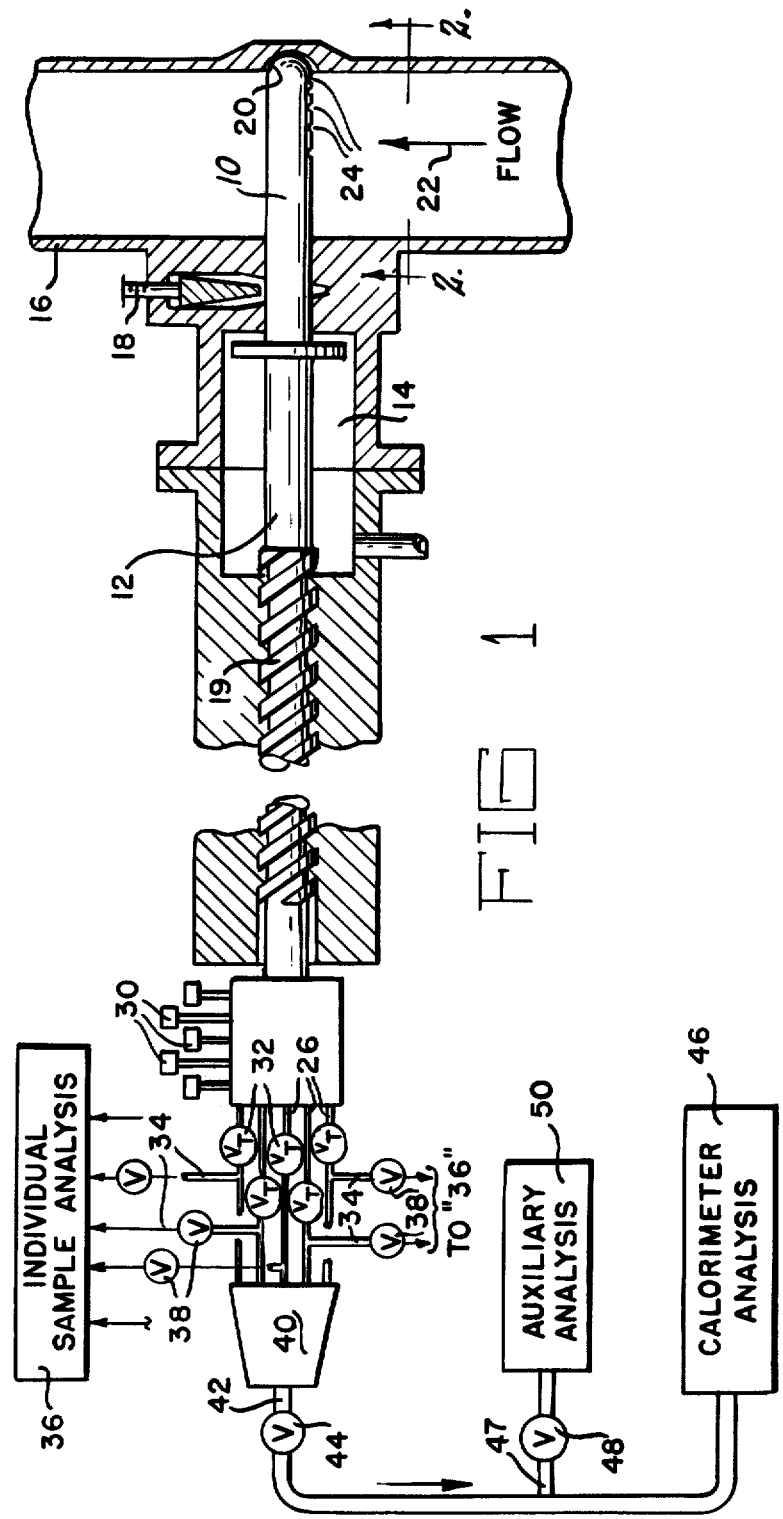

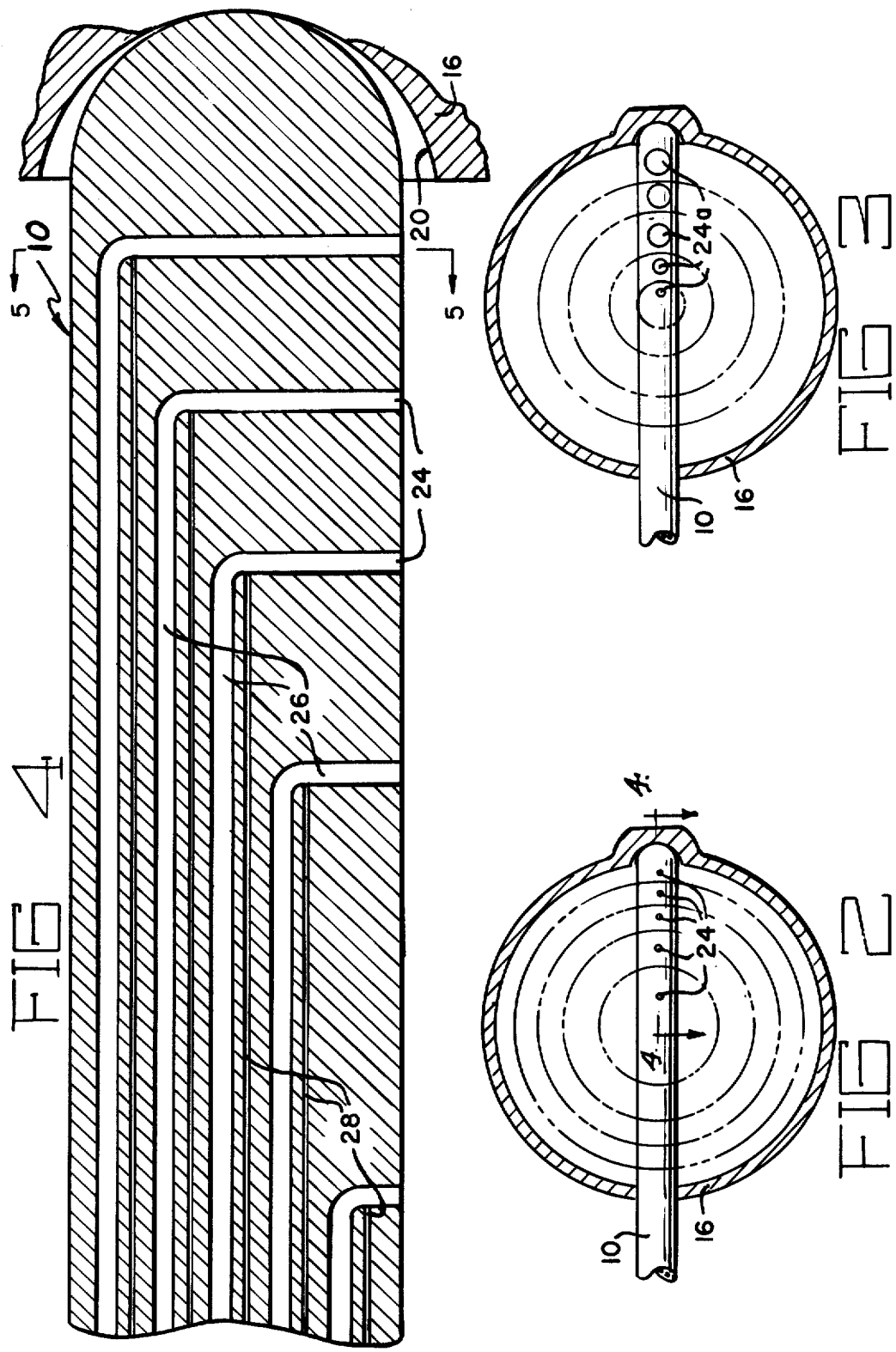

SAMPLING DEVICE FOR WITHDRAWING A REPRESENTATIVE SAMPLE FROM SINGLE AND MULTI-PHASE FLOWS

This is a continuation of application Ser. No. 173,247, filed July 29, 1980 now abandoned.

CONTRACTUAL ORIGIN OF THE INVENTION

The United States Government has rights in this invention pursuant to Contract No. EG-76-C-06-1830 between the U.S. Department of Energy and Battelle Pacific Northwest Laboratories.

BACKGROUND OF THE INVENTION

This invention concerns a device which allows a representative sample of a fluid stream to be withdrawn and desired characteristic properties analyzed. A particularly illustrative example, which we shall describe, is the application of this device to the evaluation of multi-phase fluid flow in a geothermal well stream.

Geothermal energy can be a promising alternative power source in selected parts of the world. In order to produce energy for commercial consumption, geothermal energy must be economically competitive with other conventional sources of energy. In order to attain this competitive position, the potential energy production from a candidate geothermal well must be accurately evaluated. Further, the determining characteristics of each well must be known in order to optimize equipment needs and power cycles to each well, thereby minimizing energy production costs. The geothermal well properties may be ascertained through measurement of specific chemical, physical, and thermal hydraulic parameters of the fluid flow such as phase composition, enthalpy, and mass flow rate. In carrying out these measurements, the device sampling means must withdraw a fluid specimen from the geothermal well stream such that the sample is representative of the entire fluid flow volume. Prior art has obtained fluid samples from geothermal wells via several probe configurations:

1. A single port probe fixed within pipe containing the geothermal well fluid stream (see F. A. Schraub, *Two Phase Flow Instrumentation*, Proc. of 11th National ASME/AICHE Heat Transfer Conference, August 1969, Minneapolis, Minn., pp. 47–57.)

2. A single port probe traversable across the fluid stream and retractable from the well pipe (see same reference as for no. 1).

3. A multiple port probe fixed with respect to the fluid stream and non-retractable from the stream (see R. T. Lahey, Jr., B. S. Shiralkar, and D. W. Radcliffe; *Journal of Heat Transfer*, 93, 197 (1971)).

The single port, non-retractable probe fixed within the well pipe would be suitable only for single phase flow or homogeneous multi-phase flow, neither of which exist in practice. Such a fixed probe could not examine the radial gradient of fluid flow in the pipe and would be subject to continuous exposure to the geothermal stream, resulting in substantial corrosion and erosion action.

The single port traversable probe with the retractable feature has two advantages over the fixed single port probe: the erosion and corrosion problem is greatly diminished as compared with permanent attachment inside the pipe, and the ability to traverse the probe does allow some measure of the radial gradient of fluid flow in the well pipe. However, there are inherent drawbacks to this system, including: (1) critical errors may be introduced by the speed and position control, (2) there is an inability to sample simultaneously an entire time-volume cross sectional element, (3) the moving probe results in changes in the back pressure on the sample line during the traverse which makes constant pressure sampling much more difficult, (4) at maximum extension the probe thickness must be rather large to prevent flutter or vibration and such size changes can cause misleading sampling results, and (5) since the quality and enthalpy of the mixture being withdrawn will vary during the traverse, the calorimeter analysis system will need to be designed to operate with transient inlet conditions.

Multiple-port fixed, non-etractable probes do allow sampling at a number of points in the fluid stream, thereby permitting mapping of the geothermal stream and allowing limited simultaneous sampling for the same time-volume element. Unfortunately, continuous exposure to the geothermal flow can result in enlargement or other unpredictable changes in port geometry and size. Finally, a sample representative of the entire fluid stream properties cannot be obtained by simply combining fluid samples from such a plurality of ports.

It is therefore an object of the invention to provide a fluid stream sampling device which has the ability to withdraw samples representative of the fluid stream.

It is a further object of the invention to provide a fluid stream sampling device with a plurality of sampling ports which are arranged to allow all fluid samples to be combined to produce a single sample representative of the entire fluid stream.

It is another object of the invention to provide a fluid stream sampling device which is capable of withdrawing a representative sample through a plurality of sampling ports of equal area, spaced variable distances apart, and having a constant ratio of port area to corresponding annular area sampled.

It is also an object of the invention to provide a fluid stream sampling device, which is capable of withdrawing a representative sample through a plurality of sampling ports of variable area, spaced equal distances apart, and having a constant ratio of port area to its corresponding annular area.

Additional objects, advantages and novel features of the invention will be set forth in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

This invention relates to a fluid stream sampling device for obtaining a representative sample from a multi-phase fluid stream. A retractable probe may be inserted into the fluid stream, samples withdrawn through a plurality of inlet ports, and the set of fluid samples evaluated to determine the representative characteristics of interest for the entire multi-phase, fluid stream.

BRIEF DESCRIPTION OF THE DRAWINGS

FIG. 1 illustrates supporting hardware and the sampling probe positioned within the fluid flow stream in a well pipe;

FIG. 2 shows a face view of a probe in a well pipe with a plurality of equal area ports, spaced a variable distance apart with the dashed circles depicting the annular area sampled by each port;

FIG. 3 illustrates a face view of the probe, as in FIG. 2, but with an alternate embodiment consisting of a plurality of variable area ports, equally spaced apart with the dashed circles showing the annular area sampled by each port and;

FIG. 4 shows a cross-section of the sampling probe and the internal positioning of the sampling lines of a probe with five sampling ports.

DETAILED DESCRIPTION OF THE PREFERRED EMBODIMENT

Figure 5:
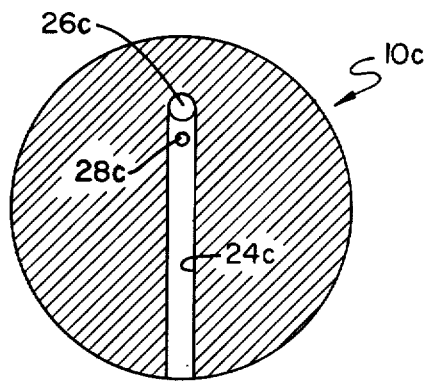
FIG. 5 shows a cross section of the probe along line 5.—5. of FIG. 4 wherein the cross-section of the probe is circular.
Figure 6:
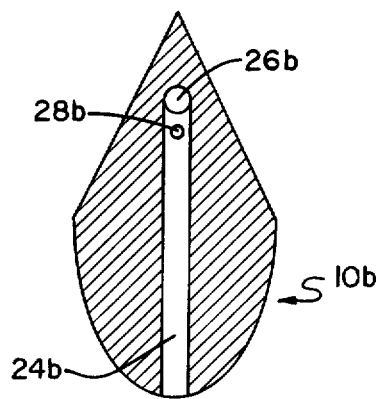
FIG. 6 shows a cross section along 5.—5. of FIG. 4 wherein the cross-section of the probe is tear-drop shaped.
Figure 7:
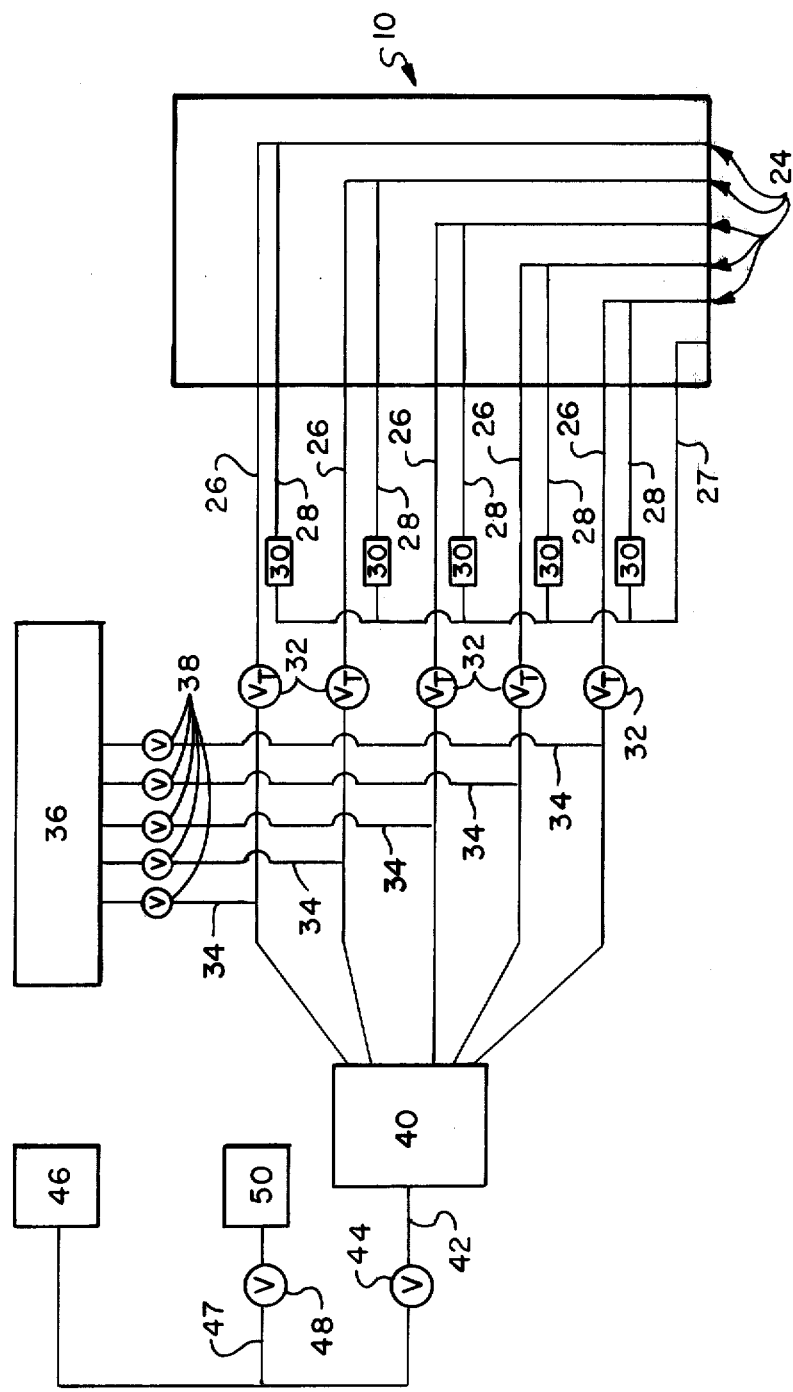

FIGS. 1–4 show the preferred embodiment of the device, as applied to the sampling of a geothermal well stream. FIGS. 5 and 6 illustrate alternative embodiments of the probe. This device also may be readily applied to obtain representative samples from other fluid streams such as water-steam mixtures in nuclear reactor coolant lines or any multi-phase fluid stream with fluid parameters having a gradient across the stream. As shown in FIG. 1, probe 10 is coupled to drive rod 12, which permits probe 10 to be driven from isolation chamber 14 into geothermal well pipe 16 by opening isolation gate valve 18, and driving the rod 12 through worm gear means 19. Probe 10 is driven to a stop against the wall of well pipe 16 into pipe recess 20, which insures accurate reproducibility of position of probe 10 in well pipe 16.

Sampling of geothermal fluid stream 22 is accomplished by withdrawal of samples through a plurality of sampling ports 24 in probe 10 positioned as shown in FIGS. 2–4. Probe 10, as shown, is a right circular cylindrical rod, but there may be other hydrodynamically favorable shapes, for example, elliptical (elongated along the direction of fluid flow), tapered or tear-drop shape. FIG. 5 is a cross-section along 5—5 of FIG. 4 showing a circular shaped probe 10c, with a port 24c, a sampling line 26c, and a static pressure tap line 28c. FIG. 6 is a cross-section along line 5.—5. of FIG. 4 showing a tear-drop shaped probe 10b with a port 24b, a sampling line 26b, and a static pressure tap line 28b. It is also important that probe 10 intercept a relatively small fraction of the total open-cross section of well pipe 16. If the probe obstructs too large a fraction of the total area, the normal fluid flow pattern may be substantially perturbed and sampling may not yield a true characteristic measure of the geothermal fluid stream 22.

In FIGS. 2 and 3, the plurality of ports 24 and 24a, respectively, are shown positioned linearly along probe 10, although these ports may, under some conditions, be positioned nonlinearly along probe 10. Ports 24 and 24a are centered on the annular zones enclosed by dashed lines such that the ratio of each port area to the area of each annular zone remains constant. In FIG. 2 is depicted the equal port area, variable spacing scheme with ports 24. In FIG. 3 is shown an alternate embodiment of the variable port area, equal spacing scheme with ports 24a. These special port geometries enable a sample representative of the entire geothermal fluid stream 22 to be withdrawn and analyzed. Typical characteristic fluid flow properties which may be determined include: mass flow rates, chemical makeup, phase gradients and percentages thereof, thermal gradients, and enthalpy and other thermal properties.

The rationale behind the special geometries shown in FIGS. 2 and 3 may be derived by considering the desired end result which is withdrawal of a sample representative of the entire geothermal fluid stream 22. To accomplish this objective, it is necessary that the sample have a direct proportionality to the mass flow rate of fluid stream 22. The total fluid mass flow rate through well pipe 16, $\dot{m}_t$, is the sum of all annular flow rates:

$$\dot{m}_t = \dot{m}_1 + \dot{m}_2 + \ldots + \dot{m}_n.$$

The mass flow rate $\dot{m}_s$ of fluid extracted by ports 24 in probe 10 is the ratio of port to annulus areas $A(s_j)/A_j$, times the particular annular flow rate, $\dot{m}_j$ summed over all annuli, $$\dot{m}_s = (A(s_1)/A_1)\dot{m}_1 + (A(s_2)/A_2)\dot{m}_2 + \ldots + (A(s_n)/A_n)\dot{m}_n$$

to provide a representative sample for the entire flow, $m_s$ must be directly relatable to the entire flow, $\dot{m}_t$. To accomplish this, $$A(s_1)/A_1 = A(s_2)/A_2 = \ldots = A(s_n)/A_n = C,$$

where C is some constant value determined by the total size of the sample desired. Applying this:

$$\dot{m}_s = C\dot{m}_1 + C\dot{m}_2 + \ldots + C\dot{m}_n$$

$$\dot{m}_s = C(\dot{m}_1 + \dot{m}_2 + \ldots + \dot{m}_n)$$

$$\dot{m}_s = C\dot{m}_t$$

For the equal port area, variable spacing scheme of FIG. 2, $$A(s_1) = A(s_2) = \ldots = A(s_n)$$

Thus in order to obtain a constant C for the ratio of port to annulus areas, the width of the annuli must be adjusted such that, $$A_1 = A_2 = \ldots = A_n$$

For this equal port area scheme, if N is equal to the number of annuli and the geothermal well pipe 16 has an internal radius of R, area of any annulus $= \pi R^2/N$
radius of the inner annulus $= r_1 = R/\sqrt{N}$
radius of the j-th annulus $= r_j = R\sqrt{j}/$
radius of N-th or outer annulus $= r_N = R$ The maximum percentage of area B which may be sampled, if one sample port 24 is placed within each annulus as shown in FIG. 2 is, $$B = 100N\pi R^2 (1 - \sqrt{(N-1)/N})^2/4\pi R^2$$

$$= 100(N - \sqrt{N^2 - N} - 0.5)$$

Therefore, for five annuli, B=1.393% and for ten annuli, B=0.66%.

In the case of the equally spaced, variable port area scheme illustrated in FIG. 3, each area of port 24a is spaced a distance R apart which is also the radial distance between consecutive annuli. In the same manner as for the equal port area, variable spacing scheme, the port areas are fixed such that the ratio of any port area to its corresponding annular area is a constant. Therefore, the flow rate of the fluid withdrawn by all the sample ports is directly proportional to the total fluid flow rate in geothermal well pipe 16. The area of each annulus in FIG. 3 is given by, $$A_1 = \pi r^2 = \pi R^2/N^2$$

$$A_2 = \pi(2r)^2 - A_1 = 3\pi r^2 = 3A_1$$

$$A_k = \pi(kr)^2 - A_{k-1} = (k^2+k)A_1/2$$

$$A_N = (N^2+N)A_1/2$$

The area of the k-th port is, $$A(s_k) = (k^2+k)A(s_1)/2 = (k^2+k)A(s_N)/(N^2+N)$$

The limiting sample port area is the outermost port, whose maximum diameter would be equal to R/N, such that its area is, $$A(s_N) = \pi R^2/4N^2$$

and the ratio of port area $A(s_N)$ to annular area $A_N$ is, $$A(s_N)/A_N = \tfrac{1}{2}N(N+1) = A(s_1)/A_1 = A(s_2)/A_2 = \ldots = A(s_k)/A_k$$

Therefore, the percentage of the total area of a well pipe cross section sampled by probe 10 for one sample port 24a in each annulus is: $25(N+2)/3N^2$ or 2.33% for five annuli and 1.00% for ten annuli.

The inlet shape of ports 24 may be straight, as shown in FIG. 4, or in special circumstances, converge or diverge just after entry into sampling lines 26. A convergent entry would correspond to sampling ports 24 having an opening like a flaired end of metal tubing, whereas a divergent entry would have a smaller diameter for ports 24 than the diameter of sampling lines 26. The most generally useful shape is the straight entry.

A divergent entry geometry for ports 24 allows precision position sampling which may be particularly useful for situations in which parameters of interest have steep gradients across the diameter of fluid stream 22. The greater diameter of sampling lines 26 enables a reasonable fluid volume to be withdrawn even though the diameter of a divergent entry for ports 24 is relatively small. The convergent entry geometry for ports 24 is more suited to sampling a fluid stream 22 with gradual changes in parameters across the diameter of fluid steam 22. A wide collection area of ports 24 would enable sampling over a larger area at one time and would minimize any problem with back pressure on sampling lines 26, which can be a problem with the divergent entry geometry for ports 24.

In order to withdraw a representative sample from geothermal fluid stream 22, ports 24 must not exert a force on the fluid being withdrawn from fluid stream 22. If sampling port forces cause suction of fluid into a particular port 24 or deflection of fluid away from a particular port 24, anomalous results will be obtained. The effect of such unbalanced fluid pressures within sampling port lines 26 in FIG. 4 will manifest itself in preferential collection of certain density of fluids, or preferred collection at certain positions along the diameter of well pipe 16. If the samples gathered from the series of sampling ports 24 are combined for evaluation of the overall average character of the fluid stream, a misleading nonrepresentative result will probably be obtained. In a geothermal well stream, numerous parameters of interest are susceptible to error from this source of nonrepresentative sampling, due to a number of such parameters having large gradients across the well pipe diameter. These gradient sensitive parameters may include mass flow rate, fluid density, thermal properties, and chemical and phase variations.

The evaluation of a geothermal well as a potential energy source is dependent on an accurate determination of these parameters which often have large gradients across the diameter of well pipe 16. For example, geothermal fluids typically have relatively low characteristic temperatures ranging from 100° C. to 300° C. At these lower temperatures, the differences between the enthalpy of the saturated liquid phase and the saturated vapor phase is substantial. Therefore, it is imperative that a sample representative of the actual proportions of liquid and vapor phases be withdrawn in order to make a correct assessment of critical geothermal well fluid properties.

In order to avoid many of these aforementioned difficulties in the representative measurement of parameters crucial to evaluation of a geothermal well stream, the technique of isokinetic sampling may be applied. The isokinetic sampling technique utilizes static pressure tap lines 28, which branch off sampling port lines 26. The fluid pressure in tap lines 28 is measured by differential pressure transducers 30, which measure the differences among the series of tap lines 28 coupled to each of sampling lines 26. As shown in FIG. 1, throttle flow control valves 32 are positioned between each of sampling port lines 26 and the various fluid analysis systems. Control valves 32 are throttled until the isokinetic static pressure in tap lines 28, as measured by differential pressure transducers 30, becomes a null value or some other predetermined value. At a null value, fluid stream 22 is sampled by ports 24 just as if ports 24 were not present, i.e., the natural flow of fluid stream 22 is measured. Other pressure conditions may be imposed to enhance removal at some positions and retard removal at others (e.g., if excessive sand flow were present near the center of the well one might reduce withdrawal there).

The isokinetic sampling technique results in withdrawal of a representative fluid sample through ports 24 into sampling port line 26. Fluid in each port line 26 may undergo individual characterization and analysis as well as an analysis of a combined average sample from all lines 26. The individual analysis may be performed by diverting samples from port lines 26 into individual sample analysis lines 34, leading to individual sample analysis system 36. Selection of fluid for analysis from lines 34 is accomplished by control valves 38, which allow one or more lines to be analyzed at one time. Analysis system 36 thus permits a point mapping of important parameters of geothermal fluid stream 22.

A combined representative sample of the entire fluid stream 22 may be obtained by termination of all port lines 26 in reservoir 40. After merging in reservoir 40, the fluid specimen passes through output line 42 through isolation valve 44 leading to several analysis systems. Calorimetry analysis is effected through calorimeter analysis system 46 in which, primarily, the enthalpy is measured. It is also possible to evaluate other fluid properties by diverting samples from output line 42 by auxiliary analysis line 47 through auxiliary isolation valve 48 to auxiliary analysis system 50. System 50 may measure any desired parameter, for example, such as chemical composition, density, or mass and volume flow rates. This system, therefore, permits complete characterization, not only of the overall properties of geothermal fluid stream 22, but also enables a detailed individual mapping of spatial and time variations of characteristic properties of fluid stream 22 in well pipe 16.

The embodiment of the invention in which an exclusive property or privilege is claimed are defined as follows:

1. A probe device for simultaneously obtaining a plurality of representative samples from a multi-phase fluid stream flowing through a well pipe, said fluid stream having a plurality of zones of pre-determined cross-sectional area to be simultaneously sampled, comprising:

a right cylindrical probe,
   drive rod means coupled to said probe which may be positioned within said fluid stream by said drive rod means, the maximum extension of said probe limited by said well pipe containing said fluid stream, said probe capable of being removed completely from said fluid stream,
   a plurality of sampling lines, each sampling line terminating in a port at the surface of said probe, said sampling ports in said probe lying along a diameter of said well pipe, each port being positioned in the probe so as to withdraw a sample from a pre-determined zone of said fluid stream, the area of each port proportional to the cross-sectional area of the zone of the fluid stream it samples,
   means for measuring the differences in static pressure among said sampling ports, said means including a plurality of static pressure tap lines branching off the sampling lines respectively, and further including a plurality of differential pressure transducers in fluid communication with said plurality of static pressure tap lines respectively, and
   a plurality of throttle means for regulating the pressure in each sampling line respectively responsive to the pressure in each static pressure tap line respectively until the differences in pressure among said static pressure tap lines are a predetermined value, whereby the sampling lines simultaneously withdraw a plurality of representative samples from said fluid stream.

2. The device of claim 1, wherein said sampling ports extend solely along a radius of said well pipe.

3. The device of claim 1, wherein said probe cross section parallel to said fluid stream is tear-drop shaped with the largest end facing into flow direction (22) of said fluid stream.

4. The device of claim 1, wherein said sampling ports have straight sides of entry into said sampling port lines.

5. The device of claim 1, wherein said sampling ports have convex sides of entry into said sampling port lines.

6. The device of claim 1, wherein said sampling ports have concave sides of entry into said sampling port lines.

7. The device of claim 1, wherein an individual analysis means is coupled to fluid samples from said sampling port lines for individual analysis, thereby providing a positional map of the characteristic properties of said fluid stream.

8. The device of claim 1 wherein said plurality of throttle means regulate the pressure in the plurality of sampling lines respectively such that the differences in pressure among said static pressure tap lines is the null value, whereby the sampling lines simultaneously withdraw a plurality of isokinetic samples from the fluid stream.

9. The device of claim 1 wherein said throttle means regulate the pressure in the sampling lines to enhance or retard sample withdrawal at selected sampling ports.

10. The device of claim 1 wherein each port is of equal area and spaced at variable distances along the probe.

11. The device of claim 1 wherein each port is of variable area and spaced at equal distances along the probe.

12. The probe device of claim 1 wherein said well pipe is provided with a recess on its inner wall, and said right cylindrical probe has a hemispherical end which may be seated in said recess of said well pipe, such that said recess limits the maximum extension of said probe into said well pipe.

* * * * *